United States Patent [19]

Odaka et al.

[11] Patent Number: 4,739,420

[45] Date of Patent: Apr. 19, 1988

[54] METHOD AND APPARATUS FOR RECORDING AND REPRODUCING A DIGITAL SIGNAL ON A RECORD MEDIUM USING A ROTARY HEAD

[75] Inventors: Kentaro Odaka, Kanagawa; Hiraku Sugiki, Saitama; Yoshimoto Ohmura, Tokyo; Takashi Ohmori, Tokyo; Makoto Yamada, Tokyo, all of Japan

[73] Assignee: Sony Corporation, Tokyo, Japan

[21] Appl. No.: 761,025

[22] Filed: Jul. 31, 1985

[30] Foreign Application Priority Data

Aug. 6, 1984 [JP] Japan ................. 59-164653

[51] Int. Cl.⁴ .............. G11B 5/584; G11B 5/09; G11B 15/467
[52] U.S. Cl. ...................... 360/77; 360/18; 360/32
[58] Field of Search ............ 360/77, 70, 32, 27, 360/18, 39, 57, 75, 10.1–10.3, 19.1, 33.1, 73

[56] References Cited

U.S. PATENT DOCUMENTS 4,528,605  7/1985  Hiraguri ................ 360/77
4,544,966  10/1985  Taniguchi ............. 360/75

FOREIGN PATENT DOCUMENTS 0113986  7/1984  European Pat. Off. ........ 360/27
0138210  10/1984  European Pat. Off.

56-68923  6/1981  Japan .................. 360/27
59-36358  2/1984  Japan.
59-2460  5/1984  Japan.

Primary Examiner—Raymond F. Cardillo
Assistant Examiner—Steven R. Garland
Attorney, Agent, or Firm—Lewis H. Eslinger; Alvin Sinderbrand

[57] ABSTRACT

In a system for recording and reproducing digital signals on a magnetic tape using a rotary head, in which the signals are recorded as a series of slanted tracks without guard bands, pilot signals that control tracking alignment of a playback head are recorded at particular positions in a specific pilot signal record region, independent of the information signal record region. Position detecting signals having various recording lengths are also recorded in the pilot signal region in such a manner that the start position of each position detecting signal corresponds substantially to the center portion of the pilot signal on an adjacent track. When the recorded tracks are reproduced by a rotary playback head having a tracing width greater than the track width, the pilot signals from the two tracks adjacent to the reproduced track on either side thereof are sampled by sampling pulses generated in response to the reproduced position detecting signal and compared in level, and the comparison output is used to control the tracking alignment of the rotary playback head.

11 Claims, 7 Drawing Sheets

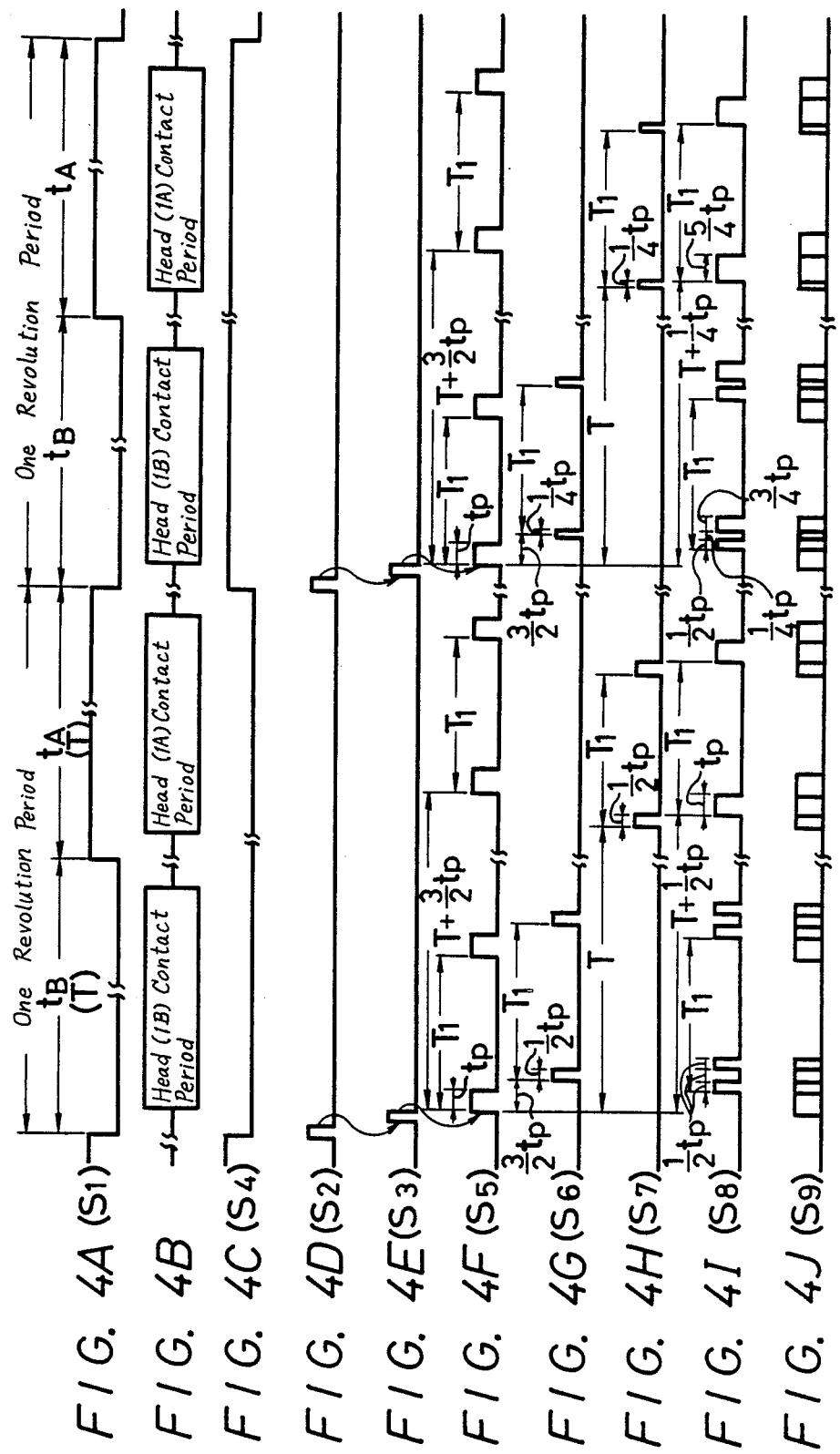

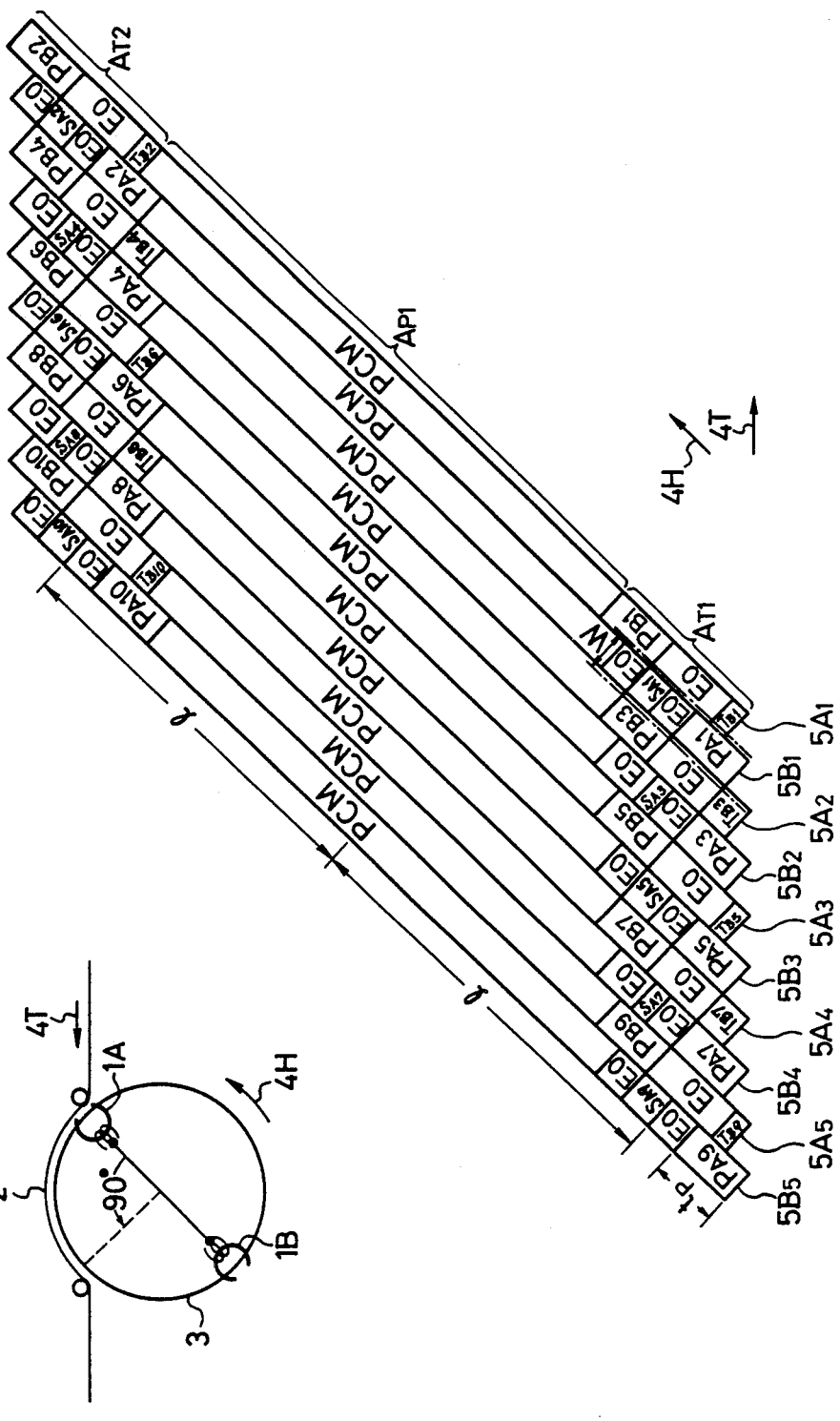

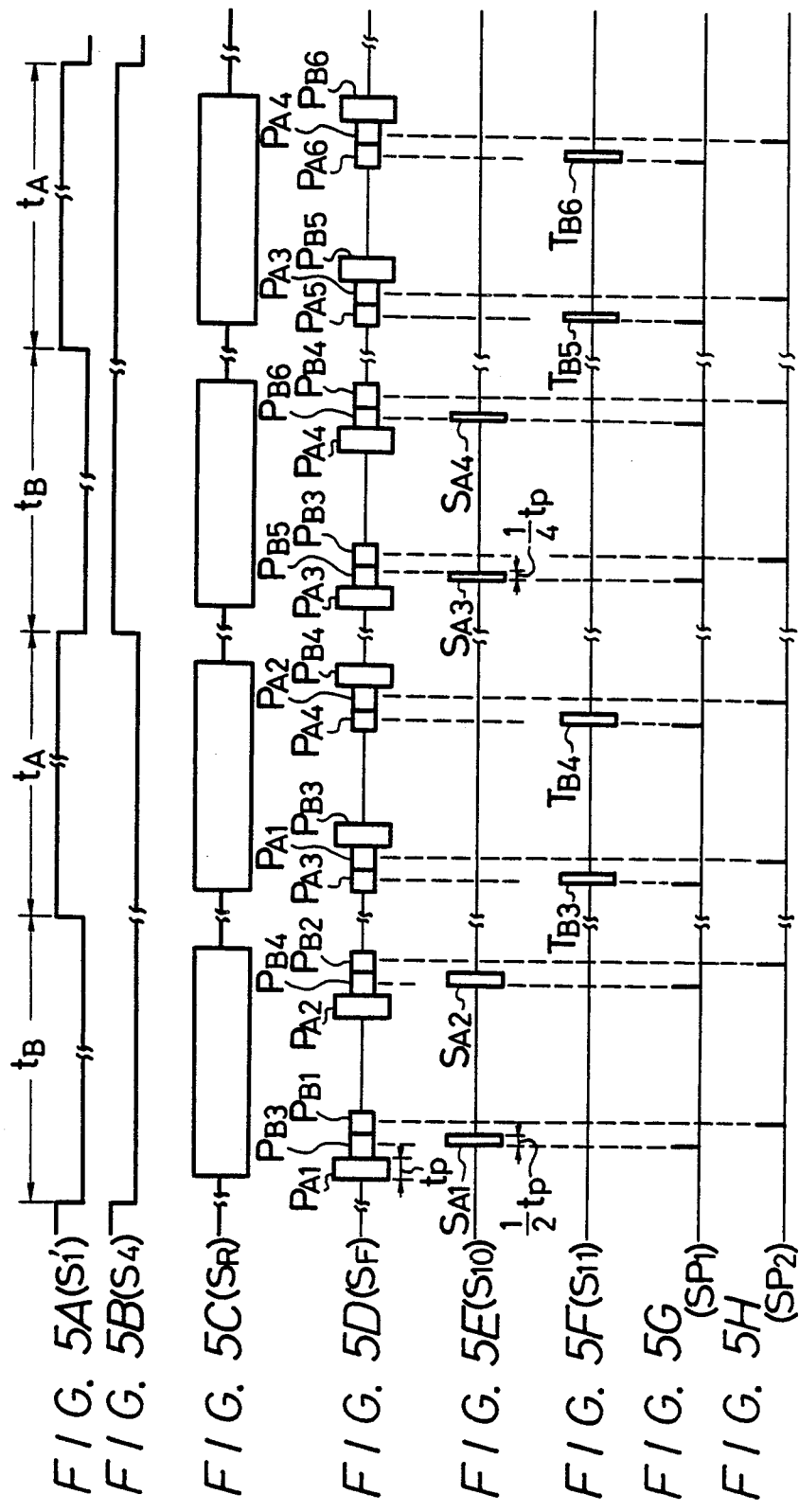

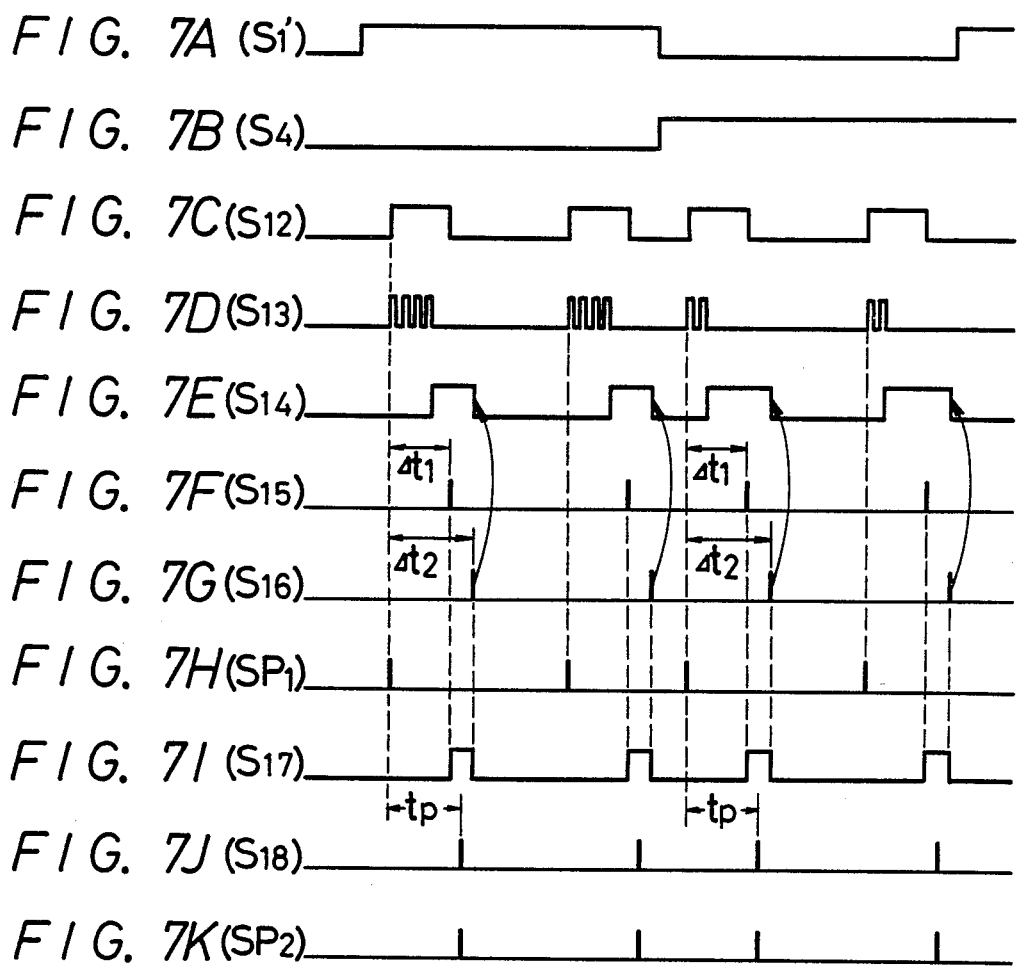

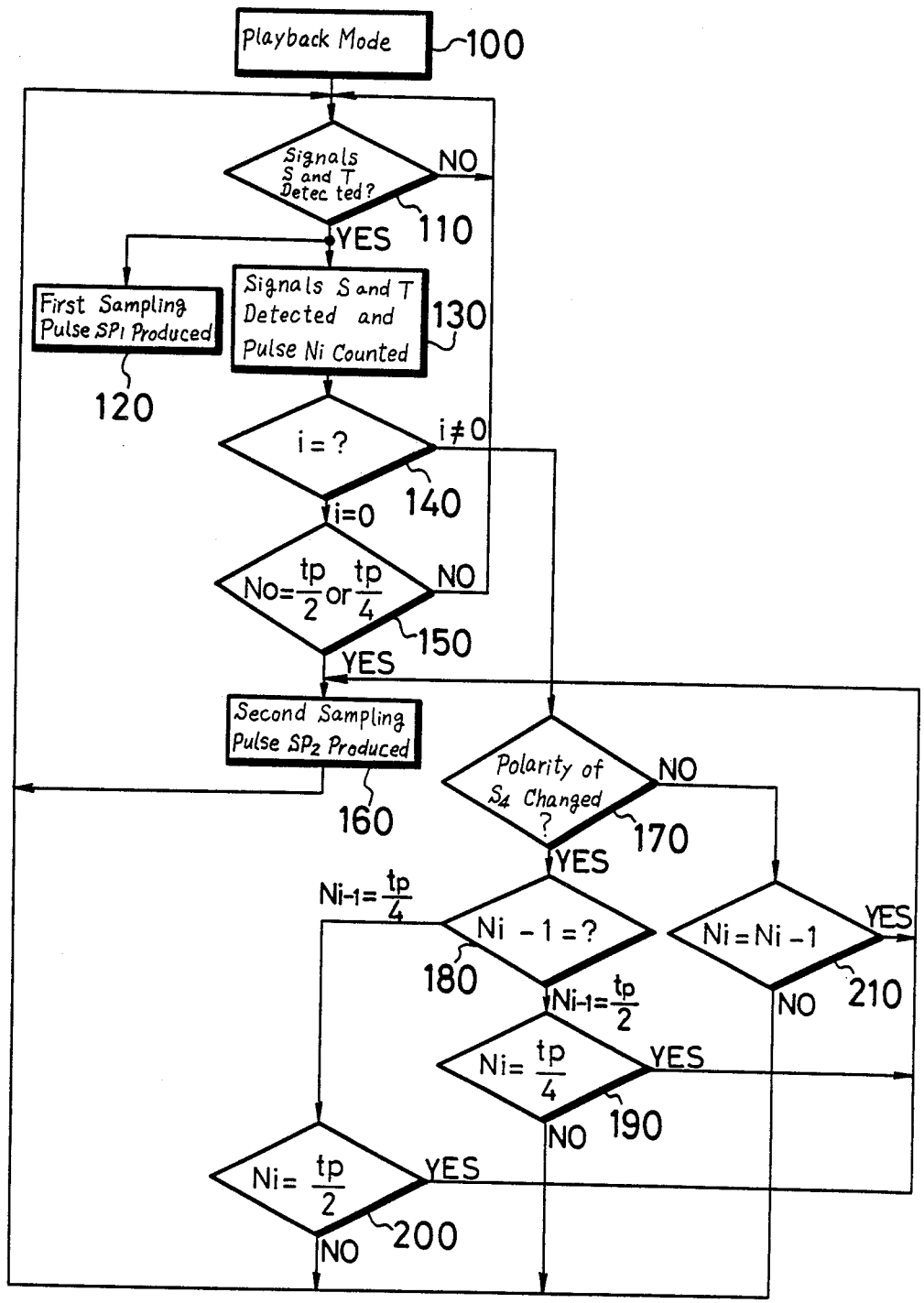

METHOD AND APPARATUS FOR RECORDING AND REPRODUCING A DIGITAL SIGNAL ON A RECORD MEDIUM USING A ROTARY HEAD

BACKGROUND OF THE INVENTION

1. Field of the Invention

This invention relates generally to a method and apparatus for recording a digital information signal and, more particularly, relates to a method and apparatus for recording a digital information signal, a pilot signal and an erase signal using a rotary head and employing the pilot signal to control tracking alignment of the rotary head during playback.

2. Description of the Prior Art

When a video signal and an audio signal are recorded on a magnetic tape using a helical-scan rotary head to form one slanted track at every unit time and then they are reproduced, it is known that the video signal and audio signal are recorded and reproduced in pulse-code modulated (PCM) form. The reason is that if the signals are pulse-code modulated, the recording and reproducing thereof can be made with high quality.

In this case, tracking control for controlling the rotary head to accurately trace the recorded tracks upon playback is typically carried out by using a control signal that has been recorded along one edge of the magnetic tape in its width direction by a fixed head. Then, this control signal is reproduced by the above fixed head during the reproduction mode and the reproduced control signal and the rotary phase of the rotary head are maintained in constant phase relation.

This known tracking control method requires the use of a special fixed magnetic head and such fixed magnetic head has a disadvantage in compact equipment, because it requires its own mounting space in the recording and reproducing apparatus.

One approach to overcoming the use of the fixed head is a proposed tracking control method that does not use such fixed magnetic head but uses only the reproduced output signal from the rotary magnetic head to carry out the tracking control for the rotary head. This tracking control method is disclosed in, for example, U.S. patent application Ser. No. 06/584313 filed Feb. 28, 1984, now U.S. Pat. No. 4,651,239, and assigned to the assignee hereof. This tracking control method relies upon the fact that it is easy to time-compress and time-expand the PCM signal and hence that it is not necessary to record and reproduce the PCM signal continuously in time, unlike an analog signal. Hence, the PCM signal and another different signal can easily be recorded on separate regions of each of the plurality of slanted tracks formed during recording.

When the PCM signal is time-compressed and magnetically recorded on a record medium by a plurality of rotary heads to form the slanted tracks with no guard bands between adjacent tracks, a plurality of tracking control pilot signals are recorded in the longitudinal direction in each track to form a record region independent of the record region for the PCM signal. Upon playback, the recorded track is traced by the rotary head having a tracing width greater than the track width, and the tracking of the rotary head is controlled by the pilot signals reproduced from the tracks adjacent the track being traced by the rotary head.

As a reference signal for recording and reproducing the tracking control pilot signal, a pulse signal (PG) having a frequency of 30 Hz is used that is indicative of the rotary phase of the head and that is generated in synchronism with the rotation of the motor that drives the rotary head.

Nevertheless, during playback when the pulse signal PG is used as a position detecting reference when the tracking pilot signal is reproduced, the reference position of the pulse signal PG can be altered or displaced due to mechanical and electrical variations in the parameters of the apparatus, caused by changes in temperature and the environment, and such variations appear as a kind of tracking error constant (offset) upon playback.

As a result, upon playback, it becomes difficult to reproduce the tracking pilot signal with the same timing as that which was present during recording, and control of the rotary head becomes imprecise. This provokes a particular disadvantage because it becomes impossible to achieve compatibility among individual units of the same kind of apparatus.

Furthermore, because the sampling pulse that is used to reproduce the tracking pilot signal over one rotational period of the rotary head is formed with the pulse signal PG as a reference, the amount of error present therein becomes integrated, so as to be increased by so-called jitter and the position of the sampling pulse is displaced in time.

To remove such shortcoming, a method and apparatus are disclosed in U.S. patent application Ser. No. 06/693,270 filed on Jan. 22, 1985, now U.S. Pat. No. 4,656,539, in which an erase signal is recorded at the position corresponding to the center of adjacent tracking pilot signals, upon playback, a sampling pulse is generated in response to this erase signal, the tracking pilot signals reproduced from the adjacent track is sampled by the sampling pulses generated and the level thereof is compared and a tracking signal for a rotary head is generated on the basis of a compared output.

OBJECTS AND SUMMARY OF THE INVENTION

It is an object of the present invention to provide an improved method and apparatus for recording a digital information signal employing a tracking control system.

It is another object of the present invention to provide an improved method and apparatus for recording a digital information signal employing a tracking control system using a pilot signal and an erase signal recorded at predetermined locations on the tracks.

According to one aspect of the present invention, there is provided a method of recording digital signals on a record medium using a rotary head that periodically traces the record medium, the method comprising the steps of:

recording a digital information signal at first predetermined areas in a plurality of slanted tracks formed on said record medium by said rotary head and forming said slanted tracks by said rotary head with no guard band between adjacent tracks;

determining second predetermined areas proximate the end of said slanted tracks and differing from said first predetermined areas;

recording a tracking pilot signal in said second predetermined areas on said slanted tracks, whereby said tracking pilot signal is available for controlling tracking alignment of a playback head during reproduction of said information signal;

determining predetermined positions in said second predetermined areas corresponding substantially to a center portion of said pilot signal on an adjacent track; and recording a position detecting signal having various recording lengths at said predetermined position in said second predetermined areas.

These and other objects, features and advantages of the present invention will become apparent from the following detailed description of the preferred embodiment taken in conjunction with the accompanying drawings, throughout which like reference numerals designate like elements and parts.

BRIEF DESCRIPTION OF THE DRAWINGS

FIG. 2 is a diagram showing an example of a rotary head assembly used in FIG. 1;

FIG. 3 is a representation of a track pattern recorded on a record medium according to the present invention;

FIGS. 4A to 4J are respectively signal waveform diagrams useful for explaining the recording operation of the embodiment of FIG. 1;

FIGS. 5A to 5H are respectively signal waveform diagrams useful for explaining the playback operation of the embodiment of FIG. 1;

FIGS. 7A to 7K are respectively signal waveform diagrams useful for explaining the operation of FIG. 6; and FIG. 8 is a flow chart useful for explaining the operation for generating a second sampling pulse.

DESCRIPTION OF THE PREFERRED EMBODIMENT

Now, an embodiment of a method and apparatus for recording a digital information signal according to the present invention will hereinafter be described in detail with reference to FIGS. 1 to 8.

Figure 1:
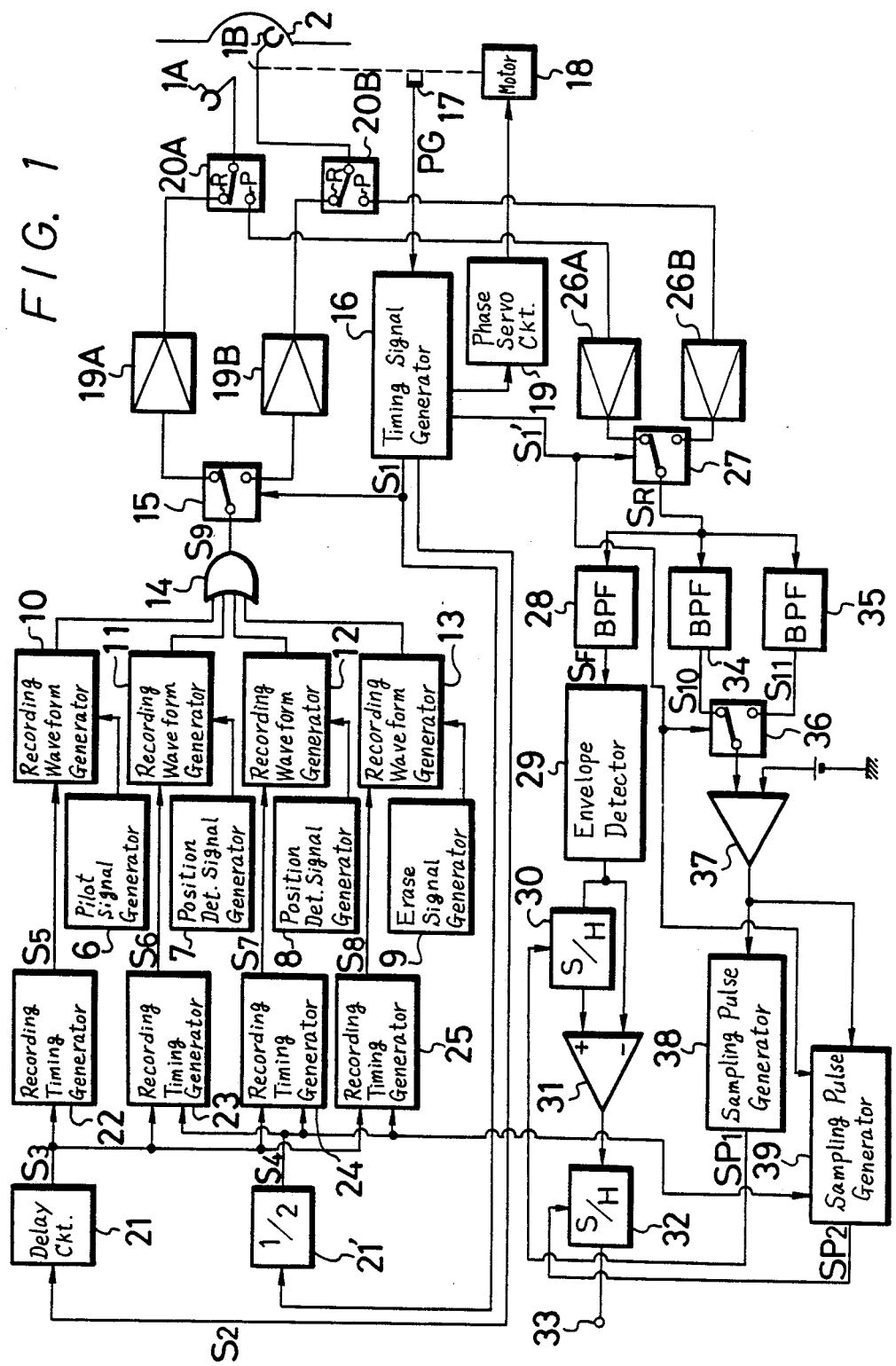
FIG. 1 is a circuit block diagram showing an embodiment of a recording apparatus according to this invention.

FIG. 1 schematically shows a circuit arrangement of an embodiment of the present invention in which only the circuit constructions, that are directly concerned with the present invention and that record and reproduce a tracking pilot signal, a position detecting signal and an erase signal, are shown. In this embodiment of the present invention, the tracking pilot signal and the erase signal are recorded and reproduced in the normal playback mode, as well as in a variable tape speed playback mode, such as when the tape speed is two or three times the normal tape speed. Thus, the circuit arrangement for recording and reproducing the information signal, such as a PCM signal, for example, is omitted, because they form no part of the present invention.

Referring to FIG. 1, rotary heads 1A and 1B are arranged in contact with a magnetic tape 2, which is used as the recording medium, and the rotary heads 1A and 1B are mounted on the periphery of a tape guide drum 3 and separated by an equal angular distance, namely, 180°, as shown in FIG. 2. In this embodiment, the magnetic tape 2 is wrapped around the outside of tape guide drum 3 at its peripheral portion with an angular spacing less than 180°, for example, an angular spacing of 90°. Rotary heads 1A and 1B are rotated at 30 revolutions per second in the direction shown by an arrow 4H, and the tape 2 is driven in the direction shown by an arrow 4T at a predetermined speed, so that slanted magnetic tracks 5A and 5B are respectively formed on the magnetic tape 2 one by one by the rotary heads 1A and 1B in a so-called overlapped writing state, as shown in FIG. 3. That is, the width (tracing width) W of the head gap is selected to be greater than the track width. In this case, the width directions of the gaps of the rotary heads 1A and 1B are made different from each other relative to the direction perpendicular to their tracing direction. In other words, the so-called azimuth angles of the rotary heads 1A and 1B are selected to be different from each other to take advantage of the azimuth effect to cancel cross-talk.

It then follows that there occurs a period in which neither of the two rotary heads 1A and 1B is in contact with the magnetic tape 2, and this period corresponds to the angular range of 90° in this embodiment. If this non-contact period is used to perform the addition of redundant data during recording and to perform error correction and the like during playback, it is possible to simplify the system.

Referring back to FIG. 1, a pilot signal oscillator or generator 6 produces a tracking pilot signal P, which has a frequency $f_0$ selected to be, for example, about 200 KHz and is recorded at a relatively high level. If the linearity between tracking phase displacement and a reproduced pilot signal output is ensured, the frequency $f_0$ of the tracking pilot signal P is desired to be a frequency presenting a relatively small amount of azimuth loss.

Position detecting signal generators 7 and 8 produce position detecting signals S and T that will detect the position of the pilot signal P. These position detecting signals S and T are also used as an erase signal for the pilot signal P. The reason is that when a new information is recorded on a magnetic tape on which the information was previously recorded while erasing the previously recorded information, it is not ascertained that the new record track is identical in location with the previous corresponding record track so that previously recorded pilot signal must be erased. The frequencies $f_1$ and $f_2$ of the position detecting signals S and T are selected to be substantially different from the frequency $f_0$ of the pilot signal P, for example, around 700 kHz and 500 kHz, respectively. Also the recording levels thereof are selected to be such as to substantially erase the pilot signal P.

Reference numeral 9 designates an oscillator or generator that generates an erase signal $E_0$. In this case, it is preferable that the erase signal $E_0$ is high in erase ratio to erase the signals P, S and T when the pilot signal P and the position detecting signals S and T are written in an overlapped writing state. The frequency $f_3$ of the erase signal $E_0$ is selected to be around 2 MHz.

Recording waveform generators 10, 11, 12 and 13 respond to an edge portion, for example, a trailing edge of a delay signal, associated with a pulse PG, which will be described in detail in the following, and produce signals as follows. The recording waveform generator 10, on the basis of the pilot signal P from the pilot signal generator 6, produces the pilot signals which are arranged with a predetermined time interval tp (tp represents the recording time interval of the pilot signal and so on) in accordance with the number of the pilot signals P to be recorded per track and the arranging manner thereof in the track with a predetermined interval. The recording waveform generators 11, 12 and 13, on the basis of the position detecting signals S and T and the erase signal $E_0$ from the generators 7, 8 and 9, produce the position detecting signals and the erase signal each of which is arranged with a predetermined time interval in accordance with the number of the position detecting signals and the erase signal recorded per track and the arranging manner thereof in the track with a predetermined interval. An OR gate circuit 14 is provided to process logically the outputs from the generators 10 to 13.

A switching circuit 15 is provided to change over the rotary heads 1A and 1B and changed in position by a switching signal $S_1$ (FIG. 4A) derived from a timing signal generator 16. The timing signal generator 16 is supplied with a pulse PG with a frequency of 30 Hz, which is indicative of the rotary phase of the rotary heads 1A and 1B, from a pulse generator 17 in synchronism with the rotation of a motor 18 that drives the rotary heads 1A and 1B. The pulse signal with a frequency of 30 Hz from the timing signal generator 16 derived from the pulse signal PG, is supplied to a phase servo circuit 19 that produces a serv output by which the rotary phase of the motor 18 is controlled.

The pilot signal and the like from the switching circuit 15 which is changed in position by the switching signal $S_1$ from the timing signal generator 16 are amplified by an amplifier 19A or 19B and then supplied through a contact R of a switching circuit 20A or 20B to the rotary head 1A or 1B thereby recorded on the magnetic tape 2. The switching circuits 20A and 20B are connected to the contact R upon recording, whereas they are connected to the contact P upon playback.

An output signal $S_2$ (FIG. 4D) from the timing signal generator 16 is supplied to a delay circuit 21 in which it is delayed with a delay time corresponding to the interval between the rotary heads 1A, 1B and the mounting position of the pulse generator 17, and the like. A delayed output signal $S_3$ (FIG. 4E) from the delay circuit 21 is fed to each of recording timing generators 22 to 25. The switching signal $S_1$ from the timing signal generator 16 is frequency-divided to $\frac{1}{2}$ by a frequency divider 21' to become a signal $S_4$ (FIG. 4C) which then is fed to the timing generators 23 to 25. The recording timing generators 22 to 25 generate timing signals which are used as recording references for pilot signal and the like. In this case, the trailing edge of the signal $S_3$ (FIG. 4E) delayed by the delay circuit 21 is made coincident with the time at which the first rotary head comes in contact with the tape during one rotation period.

The recording timing generator 22 produces a signal $S_5$ (FIG. 4F) which is synchronized with the trailing edge of the signal $S_3$ during the half rotation period of one head, for example, the half rotation period of the head 1B and which is delayed by time $T+3/2tp$ (T represents the time corresponding to the half rotation period of the head) from the trailing edge of the signal $S_3$ during the half rotation period of the other head with a predetermined interval $T_1$ and whose duration time is tp. The recording timing generator 23 generates a signal $S_6$ (FIG. 4G) delayed by time $3/2tp$ from the trailing edge of the signal $S_6$ during only the half rotation period of one head, for example, during only the half rotation period of the head 1B with a predetermined interval $T_1$: where during, for example, the odd rotation period of the head, the duration time of the signal $S_6$ is $\frac{1}{2}tp$, while during the even rotation period of the head, the duration time thereof is $\frac{1}{4}tp$. The recording timing generator 24 generates a signal $S_7$ (FIG. 4H) delayed from the trailing edge of the signal $S_3$ by time T during only the half rotation period of the other head, for example, only the half rotation period of the head 1A with a predetermined interval $T_1$ where the duration time is $\frac{1}{4}tp$ during the odd rotation period of the head, while the druation time is $\frac{1}{2}tp$ during the even rotation period of the head. The recording timing generator 25 generates the following signal $S_8$. That is, in the odd rotation period of the head and during the half rotation period of one head, there are generated a pair of pulses which are delayed by time tp from the trailing edge of the signal $S_3$ with an interval of time $\frac{1}{2}tp$ therebetween and at a predetermineed interval $T_1$ and each of which pulses has the duration time of $\frac{1}{2}tp$, while during the other half rotation period of the head, there is generated a signal having a duration time tp and delayed by time $T+\frac{1}{2}tp$ from the trailing edge of the signal $S_3$ at a predetermined interval $T_1$. On the other hand, in the even rotation period of the head and during the half rotation period of one head, there are generated a pair of pulses delayed by a time $\frac{1}{2}tp$ from the trailing edge of the signal $S_3$ whose duration times are respectively $\frac{1}{2}tp$ and $\frac{3}{4}tp$ with an interval of $\frac{1}{4}tp$ at a predetermined interval $T_1$, while during the half rotation period of the other head, there is generated a signal delayed by a time $T+\frac{1}{2}tp$ from the trailing edge of the signal $S_3$ and whose duration time is $5/4tp$ at a predetermined interval $T_1$ (refer to FIG. 4I).

The signal $S_5$ (FIG. 4F), the signal $S_6$ (FIG. 4G), the signal $S_7$ (FIG. 4H) and the signal $S_8$ (FIG. 4I) from the recording timing generators 22, 23, 24 and 25 are respectively supplied to the recording waveform generators 10, 11, 12 and 13 substantially as their gate signals so that the pilot signal P, the position detecting signals S and T and the erase signal $E_0$ from the generators 6, 7, 8 and 9 are respectively supplied through the recording waveform generators 10, 11, 12 and 13 to the OR gate circuit 14 as shown in FIG. 1. Thus, they are developed at the output side thereof as a composite signal $S_9$ (FIG. 4J).

In FIG. 1, amplifiers 26A and 26B are respectively supplied with the playback outputs from the corresponding rotary heads 1A and 1B when the switching circuits 20A and 20B are changed in position to their contacts P upon playback. The respective outputs of these amplifiers 26A and 26B are supplied to a switching circuit 27. The switching circuit 27 is alternately changed in position by a switching signal $S_1'$ (FIG. 5A) of 30 Hz from the timing signal generator 16 during the half rotation period including the tape contact period of the head 1A and during the half rotation period including the tape contact period of the head 1B similarly to the recording mode, respectively.

A band pass filter 28 of a narrow band having a center pass frequency $f_0$ is provided to derive only the pilot signal P from the reproduced output of the switching circuit 27. An envelope detector 29 is provided to envelope-detect the output from the band pass filter 28 and the output from the envelope detector 29 is sampled and then held by a sample-and-hold circuit 30. A comparator or differential amplifier 31 is provided to compare the outputs from the envelope detector 29 and the sample-and-hold circuit 30. A sample-and-hold circuit 32 is provided to sample and hold the compared error signal from the differential amplifier 31. These sample-and-hold circuits 30 and 32 function to sample and hold a crosstalk component of the pilot signals recorded on both end portions of the tracks adjacent to the track being traced upon normal playback mode as will be described later. Then, the output from the sample-and-hold circuit 32 is delivered to an output terminal 33 as a tracking control signal.

In order to form the sampling pulse and the like for the sample-and-hold circuits 30 and 32, band pass filters 34 and 35 of narrow band having center pass frequencies $f_1$ and $f_2$ are provided at the output side of the switching circuit 27 which derive only the position detecting signals S and T from the reproduced output. Outputs $S_{10}$ (FIG. 5E) and $S_{11}$ (FIG. 5F) thereof are supplied through a switching circuit 36 to a comparator 37 which is served as a waveform shaping circuit. Similarly to the switching circuit 27, the switching circuit 36 is changed in position by the switching signal $S_1'$ of 30 Hz from the timing signal generator 16.

Sampling pulse generators 38 and 39 are provided at the output side of the comparator 37. The sampling pulse generator 38 generates a first sampling pulse $SP_1$ (FIG. 5G) in synchronism with the leading edge of the output from the comparator 37, whereas the sampling pulse generator 39 generates a second sampling pulse $SP_2$ (FIG. 5H) with the delay of a predetermined time $t_P$ after the first sampling pulse $SP_1$ was produced. These sampling pulses $S_{P1}$ and $SP_2$ are supplied to the sample-and-hold circuits 30 and 32, respectively.

Next, the circuit operation of FIG. 1 will be described with reference to the signal waveforms shown in FIGS. 4 to 5.

Upon recording, in response to the pulse PG indicative of the rotary phases of the rotary heads 1A and 1B derived from the pulse generator 17, the timing signal generator 16 produces the signal $S_2$ shown in FIG. 4D. This signal $S_2$ is supplied to and delayed by a predetermined time by a delay circuit 21 and so the delay circuit 21 produces at its output side the signal $S_3$ shown in FIG. 4E. This signal $S_3$ is supplied to the recording timing generators 22 to 25 as mentioned above so that the recording timing generator 22 produces at its output side the signal $S_5$ shown in FIG. 4F. The switching signal $S_1$ from the timing signal generator 16 is supplied to the frequency divider 21' so that the frequency divider 21' produces at its output side the signal $S_4$ shown in FIG. 4C. This signal $S_4$ is supplied to the recording timing generators 23 to 25 whereby in response to the signals $S_3$ and $S_4$, the recording timing generators 23 to 25 produce at their output sides the signals $S_6$ to $S_8$ shown in FIGS. 4G to 4I, respectively.

The signals $S_5$, $S_6$, $S_7$ and $S_8$ are respectively supplied to the recording waveform generators 10, 11, 12 and 13. Thus, the recording waveform generator 10 passes therethrough in synchronism with the signal $S_5$ supplied thereto the pilot signal P from the oscillator or generator 6 at a predetermined interval and for a predetermined time $t_P$ as shown in FIG. 4F, the recording waveform generator 11 passes therethrough in synchronism with the signal $S_6$ supplied thereto the position detecting signal S from the oscillator 7 at a predetermined interval and for a predetermined time as shown in FIG. 4G, the recording waveform generator 12 passes therethrough in synchronism with the signal $S_7$ supplied thereto the position detecting signal T from the oscillator 8 at a predetermined interval and for a predetermined time as shown in FIG. 4H, and the recording waveform generator 13 passes therethrough in synchronism with the signal $S_8$ supplied thereto the erase signal $E_0$ from the oscillator 9 at a predetermined interval and for a predetermined time as shown in FIG. 4I.

The output signals from the recording waveform generators 10 to 13 are added together by the OR circuit 14 which then produces at its output side the signal $S_9$ shown in FIG. 4J.

By the way, at this time, let it be considered that for example, the head 1B records the track $5B_1$ in FIG. 3 (in the first half period tB of FIG. 4). Then, the first and second pulses of the signal $S_5$ in FIG. 4F correspond to the pilot signals $P_{A1}$ and $P_{A2}$, respectively, the first and second pulses of the signal $S_6$ in FIG. 4G correspond to the position detecting signals $S_{A1}$ and $S_{A2}$, respectively, and the first and second pulses formed of a pair of pulses of the signal $S_8$ in FIG. 4I correspond to the erase signals $E_0$ which are adjacent to the both sides of the position detecting signals $S_{A1}$ and $S_{A2}$, respectively. Accordingly, signals composed of the signals corresponding to the alignments of these signals, namely, $P_{A1}$, $E_0$, $S_{A1}$, $E_0$ and $P_{A2}$, $E_0$, $S_{A2}$ and $E_0$ are produced at each group at the output side of the OR circuit 14.

Let it be considered that for example, the head 1A records the track $5A_2$ in FIG. 3 (in the first half period tA of FIG. 4). Then, the first and second pulses of the signal $S_5$ in FIG. 4F respectively correspond to the pilot signals $P_{B3}$ and $P_{B4}$, the first and second pulses of the signal $S_7$ in FIG. 4H respectively correspond to the position detecting signals $T_{B3}$ and $T_{B4}$, and the first and second pulses of the signal $S_8$ in FIG. 4I respectively correspond to the erase signals $E_0$ which are adjacent to the one sides of the position detecting signals $T_{B3}$ and $T_{B4}$. Then, the signals composed of tne signals corresponding to the alignments of these signals, namely, $T_{B3}$, $E_0$, $P_{B3}$ and $P_{B4}$, $E_0$ and $P_{B4}$ are produced at each group at the output side of the OR circuit 14.

Further, let it be considered that for example, the head 1B records the track $5B_2$ in FIG. 3 (the second half period tB of FIG. 4). The first and second pulses of the signal $S_5$ in FIG. 4F respectively correspond to the pilot signals $P_{A3}$ and $P_{A4}$, the first and second pulses of the signal $S_6$ in FIG. 4G respectively correspond to the position detecting signals $S_{A3}$ and $S_{A4}$, and the first and second pulse formed of a pair of pulses of the signal $S_8$ in FIG. 4I respectively correspond to the erase signals $E_0$ which are adjacent to the both sides of the position detecting signals $S_{A3}$ and $S_{A4}$. The signals composed of the signals corresponding to the alignment of these signals, namely, $P_{A3}$, $E_0$, $S_{A3}$ and $E_0$ and $P_{A4}$, $E_0$, $S_{A4}$ and $E_0$ are produced at each group at the output side of the OR circuit 14.

Furthermore, let it be considered that for example, the head 1A records the track $5A_3$ in FIG. 3 (the second half period tA of FIG. 4). Then, the first and second pulses of the signal $S_5$ in FIG. 4F correspond to the pilot signals $P_{B5}$ and $P_{B6}$, respectively, the first and second pulses of the signal $S_7$ in FIG. 4H respectively correspond to the position detecting signals $T_{B5}$ and $T_{B6}$, and the first and second pulses of the signal $S_8$ in FIG. 4I respectively correspond to the erase signals $E_0$ which are adjacent to the one sides of the position detecting signals $T_{B5}$ and $T_{B6}$. The signals composed of the signals corresponding to the alignments of these signals, namely, $T_{B5}$, $E_0$ and $P_{B5}$ and $T_{B6}$, $E_0$ and $P_{B6}$ are produced at each group at the output side of the OR circuit 14.

On the other hand, from the timing signal generator 16, there is produced the switching signal $S_1$ as shown in FIG. 4A in response to the pulse PG from the pulse generator 17. This signal $S_1$ is in synchronism with the rotation of the rotary heads 1A and 1B so that as shown in FIGS. 4A and 4B, during the half rotation period tA of the head in which the signal $S_1$ is at high level, the head 1A comes in contact with the tape 2, while during the half rotation period tB in which the signal $S_1$ is at low level, the head 1B comes in contact with the tape 2. Then, the switching circuit 15 is changed in position by the switching signal $S_1$ to the state shown in FIG. 1 during the period tA, while it is changed in position to the state opposite to that shown in the figure during the period tB, thus the head being changed over.

Accordingly, when the switching circuit 15 is in the position opposite to that shown in FIG. 1, the signal $S_9$ obtained at the output side of the OR circuit 14 is supplied through the amplifier 19B and the contact R of the switching circuit 20B to the head 1B, whereby at the beginning and the end of the contact period of the head 1B with the tape 2 within the period tB and in record regions $A_{T1}$ and $A_{T2}$ for the tracking signal provided at both end portions of the track 5B in its longitudinal direction distant from the center position of the track 5B in its longitudinal direction by an equal length l, the signal $S_9$ is recorded in the odd rotation period of the head (the first half period tB of FIG. 4) for a time, $tp + \frac{1}{4}tp + \frac{1}{4}tp + \frac{1}{4}tp$ and a time $tp + \frac{1}{4}tp + \frac{1}{4}tp + \frac{1}{4}tp$, while it is recorded thereon in the even rotation period of head (the second half period tB of FIG. 4), for a time $tp + \frac{1}{4}tp + \frac{1}{4}tp + \frac{1}{4}tp$ and a time $tp + \frac{1}{4}tp + \frac{1}{4}tp + \frac{1}{4}tp$, respectively.

On the other hand, when the switching circuit 15 is in the state as shown in FIG. 1, the signal $S_9$ is supplied through the amplifier 19A and the contact R of the switching circuit 20A to the head 1A, whereby at the beginning end and the end of the contact period of the head 1A with the tape 2 within the period tA and in the similar regions $A_{T1}$ and $A_{T2}$ provided in the both end portions of the track 5A in its longitudinal direction distant from the central position of the track 5A in its longitudinal direction by the equal distance l, the signal $S_9$ is recorded in the odd rotation period (the first half period tA of FIG. 4) of the head for a time $\frac{1}{4}tp + tp + tp$ and a time $\frac{1}{4}tp + tp + tp$, while it is recorded in the even rotation period (the second half period tA of FIG. 4) of the head, for a time $\frac{1}{4}tp + 5/4tp + tp$ and a time $\frac{1}{4}tp + 5/4tp + tp$, respectively.

In other times than those within which these pilot signals, the position detecting signals and the erase signals are recorded, though not shown, an audio PCM signal of one segment portion to be recorded as one track is supplied through the amplifier 19A to the head 1A during the period tA, while it is supplied through the amplifier 19B to the head 1B during the period tB so that they are recorded on the record region $A_{P1}$ other than the record regions of the above-described pilot signals of the respective tracks 5A and 5B.

The reproduction of the signals recorded as mentioned above will be described hereinafter.

Also in this playback mode, the motor 18 is applied with the phase servo from the phase servo circuit 19 similarly to the recording mode.

The signals reproduced from the tape 2 by the rotary heads 1A and 1B are respectively supplied through the contact P of the switching circuit 20A and the amplifier 26A and the contact P of the switching circuit 20B and the amplifier 26B to the switching circuit 27. This switching circuit 27 is alternately changed over by the switching signal $S_1'$ of 30 Hz as shown in FIG. 5A from the timing signal generating circuit 16 at the half rotation period tA including the tape contact period of the head 1A and at the half rotation period tB including the tape contact period of the head 1B similarly to the recording mode. Accordingly, from this switching circuit 27 there is derived an intermittent PCM signal $S_R$ of one segment each as shown in FIG. 5C. Then, though not shown this PCM signal $S_R$ is supplied to a playback processor to thereby be demodulated to the original PCM signal and then further fed to a decoder in which a data of each block is detected by the block synchronizing signal, corrected for error and de-interleaved and then reconverted to the analog audio signal by the D/A converter and then fed to the output side.

The tracking control will be carried out as follows.

If, now, the head 1B traces the range of a tracing width W including the track $5B_1$ as shown by one-dot chain lines in FIG. 3, the head 1B traces also the tracks $5A_2$ and $5A_1$ which are adjacent to this track $5B_1$ so that as shown in FIG. 3, in the region $A_{T1}$, the pilot signal $P_{A1}$ of the track $5B_1$, the pilot signal $P_{B3}$ of the adjacent track $5A_2$ and the pilot signal $P_{B1}$ of the adjacent track $5A_1$ are reproduced by the head 1B, while in the region $A_{T2}$, the pilot signal $P_{A2}$ of the track $5B_1$, the pilot signal $P_{B4}$ of the track $5A_2$ and the pilot signal $P_{B2}$ of the adjacent track $5A_1$ are reproduced by the head 1B, respectively. At this time, the reproduced output of the head 1B derived from the switching circuit 27 is supplied to the band-pass filter 28 of the narrow pass band having the pass center frequency $f_0$ which then passes therethrough only the pilot signals as its output $S_F$ as shown in FIG. 5D and this output signal $S_F$ is fed to the envelope detector 29.

The output $S_R$ of the switching circuit 27 is also supplied to the band-pass filters 34 and 35 of the narrow pass bands having pass center frequencies $f_1$ and $f_2$ which then pass therethrough at their output sides the position detecting signals $S_{10}$ and $S_{11}$ as shown in FIGS. 5E and 5F, respectively. These signals $S_{10}$ and $S_{11}$ are respectively supplied to the switching circuit 36 from which the signal $S_{10}$ is derived when the switching signal $S_1'$ is at low level and the signal $S_{11}$ when it is at high level which then are fed to the comparator 37.

The comparator 37 compares the signals $S_{10}$ and $S_{11}$ supplied thereto with a reference value, waveform-shapes them and supplies the same to the sampling pulse generators 38 and 39. The sampling pulse generator 38 produces the first sampling pulse $S_{P1}$ in synchronism with the rising-up edge of the wave-form-shaped signal $S_{10}$ as shown in FIG. 5G and this first sampling pulse $S_{P1}$ is supplied to the sample-and-hold circuit 30. At this time, as will be clear from FIG. 5, the sampling pulse $S_{P1}$ makes the sample-and-hold circuit 30 sample the crosstalk components of the pilot signals $P_{B4}$ and $P_{B4}$ of the adjacent track $5A_2$ at the side opposite to the transportation direction of the tape 2 shown by an arrow 4T (FIG. 3) and the signal thus sampled is supplied to one input terminal of the differential amplifier 31 as the tracking signal of advanced phase.

After the time tp since the sampling pulse $S_{P1}$ was produced, the crosstalk component of the pilot signals $P_{B1}$ and $P_{B2}$ of the adjacent track $5A_1$ at the side of the tape transport direction is supplied to the other input terminals of the differential amplifier 31 from the envelope detector 29 as the tracking signals of delayed phase, respectively. Accordingly, the differential amplifier 31 compares the tracking signals corresponding to the crosstalk components of the pilot signals $P_{B3}$, $P_{B1}$, and $P_{B4}$, $P_{B2}$, in turn.

Then, the compared error signal from the differential amplifier 31 is supplied to the sample-and-hold circuit 32 in which it is sampled by the sampling pulse $S_{P2}$ produced from the sampling pulse generator 39 after the time tp since the sampling pulse $S_{P1}$ was produced. Consequently, from the sample-and-hold circuit 32, the difference between the two inputs to the differential amplifier 31 is produced as the tracking control signal. This tracking control signal is supplied from the output terminal 33 to a capstan motor (not shown) which then controls the transported amount of the tape. Thus, the head 1B is controlled so that the level difference between the two inputs to the differential amplifier 31 becomes zero or when the head 1B traces the track $5B_1$, the head 1B traces the two tracks $5A_2$ and $5A_1$ at both sides of the track $5B_1$ with the same amount. In other words, the head 1B is controlled to trace the track $5B_1$ in such a way that the central position of the width direction of the gap of the head 1B is made coincident with the central position of the track $5B_1$.

As to the other tracks, the heads will be controlled similarly. For example, when the head 1A traces the track $5A_2$, there are obtained the crosstalk components of the pilot signals $P_{A3}$, $P_{A4}$, and $P_{A1}$, $P_{A2}$ of the adjacent tracks $5B_2$ and $5B_1$. Thus, the crosstalk components of the pilot signals $P_{A3}$ and $P_{A4}$ are sampled by the sampling pulse $S_{P1}$ supplied from the sampling pulse generator 38 to the sample-and-hold circuit 30 to thereby produce the tracking signal. This tracking signal is supplied to the differential amplifier 31 at the next stage and the output corresponding to the crosstalk components of the pilot signals $P_{A1}$ and $P_{A2}$ and derived from the envelope detector 29 is supplied to the differential amplifier 31 in which the tracking signals respectively corresponding to the crosstalk components between the pilot signals $P_{A1}$ and $P_{A2}$ and $P_{A4}$ and $P_{A2}$ are compared with one another. The compared error signal is sampled by the sampling pulse $SP_2$ which is supplied to the sample-and-hold circuit 32 so as to produce the tracking control signal for the head 1A.

Similarly, when the head 1B traces the track $5B_2$, as shown in FIG. 3, the crosstalk components of the pilot signals $P_{B5}$, $P_{B6}$ and $P_{B3}$, $P_{B4}$ of the adjacent tracks $5A_3$ and $5A_2$ are produced. Thus, the crosstalk components of the pilot signals $P_{B5}$ and $P_{B6}$ are sampled by the sampling pulse $SP_1$, the tracking signals corresponding to the crosstalk components of the pilot signals $P_{B5}$, $P_{B3}$ and $P_{B6}$, $P_{B4}$ are compared with one another by the differential amplifier 31. Finally, the compared error signal is sampled by the sampling pulse $SP_2$ to thereby produce the tracking control signal for the head 1B.

Similarly, when the head 1A traces the track $5A_3$, as shown in FIG. 3, the crosstalk components of the pilot signals $P_{A5}$, $P_{A6}$ and $P_{A3}$, $P_{A4}$ of both the adjacent tracks $5B_3$ and $5B_2$ are produced. Thus the crosstalk components of the pilot signals $P_{A5}$ and $P_{A6}$ are sampled by the sampling pulse $SP_1$ and the tracking signals corresponding to the crosstalk components of the pilot signals $P_{A5}$, $P_{A3}$ and $P_{A6}$, $P_{A4}$ are controlled by the differential amplifier 31. Finally, the compared error signal is sampled by the sampling pulse $SP_2$ to thereby produce the tracking control signal corresponding to the head 1A.

Figure 6:
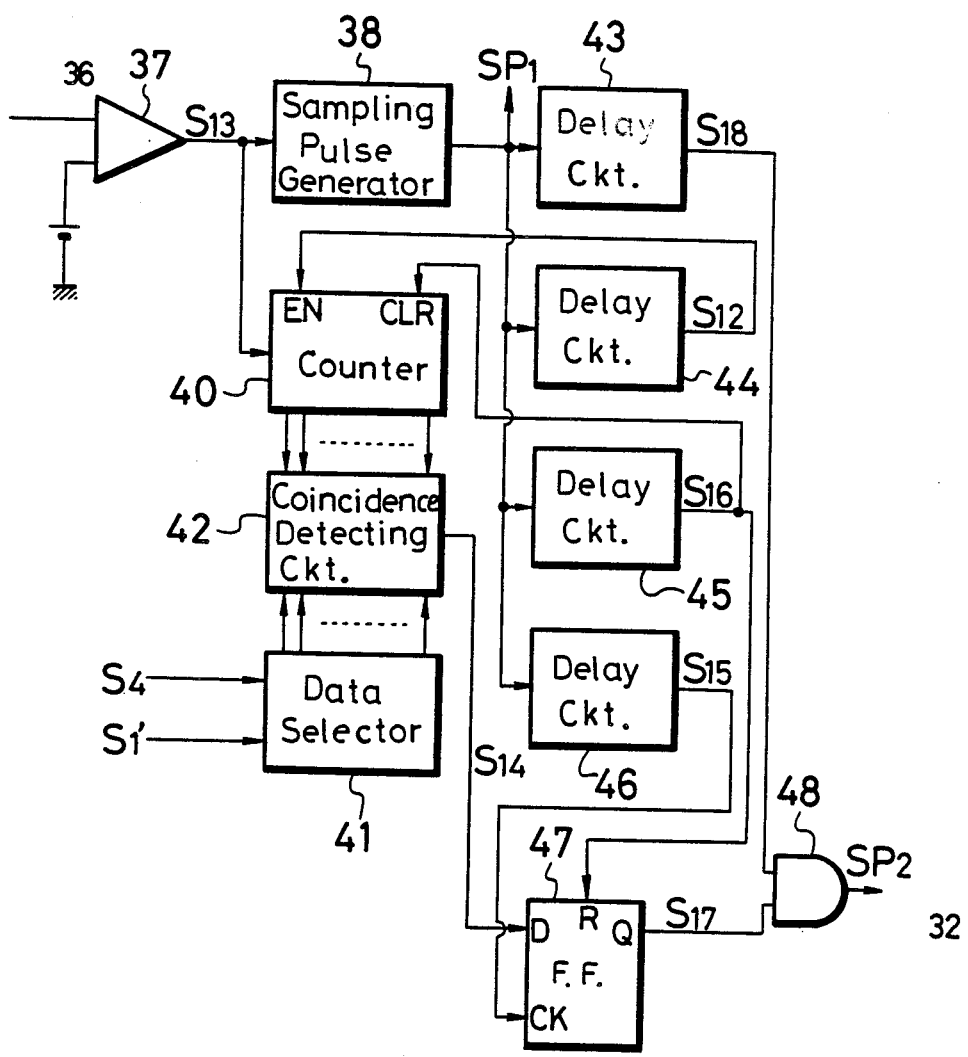
FIG. 6 is a circuit diagram showing an example of a main part of the present invention.

FIG. 6 shows an example of a practical circuit arrangement of the sampling pulse generator 39. In the figure, reference numeral 40 designates a counter for counting the pulses of the position detecting signal supplied thereto from the comparator 37. Reference numeral 41 designates a data selector which is responsive to the signals $S_4$ and $S_1'$ and then selects the data (set values) of four kinds which are classified by the contents of the position detecting signals, namely, classified by the frequencies and the recording lengths of the position detecting signals S and T in this embodiment. Reference numeral 42 designates a coincidence detecting circuit for detecting whether the count value of the counter 40 coincides with the data of the data selector 41. As this coincidence detecting circuit 42, there is used, for example, a digital comparator.

Reference numerals 43 to 46 respectively designate delay circuits each of which derives a predetermined delay signal from the sampling pulse $SP_1$. The counter 40 is enabled by the output from the delay circuit 44 and is then cleared by the output from the delay circuit 45. Reference numeral 47 designates a D-type flip-flop circuit and to an input terminal D of this flip-flop circuit 47, there is supplied the output from the coincidence detecting circuit 42. To a clock terminal CK of the flip-flop circuit 47, there is substantially applied the sampling pulse $SP_1$ through the delay circuit 46 and to a reset terminal R thereof, there is supplied the output of the delay circuit 45.

Reference numeral 48 designates a gate circuit, for example, an AND circuit. To one input terminal of this AND circuit 48, there is supplied the output of the delay circuit 43, while to the other input terminal thereof, there is supplied the output developed at an output terminal Q of the flip-flop circuit 47. Then, the sampling pulse $SP_2$ is produced at the output terminal thereof.

The operation of the sampling pulse generator 39 shown in FIG. 6 will be described with reference to the signal waveform diagram of FIG. 7.

When a signal $S_{13}$ as the position detecting signal, shown in FIG. 7D is supplied from the comparator 37 to the sampling pulse generator 38, this sampling pulse generator 38 produces the sampling pulse $SP_2$ in synchronism with the leading edge of the first pulse of the signal $S_{13}$ shown in FIG. 7H. This sampling pulse $SP_1$ is supplied to the above-described sample-and-hold circuit 30 (FIG. 1) and also to the delay circuits 43 to 46.

The delay circuit 44 produces at its output side a signal $S_{12}$ having a duration time corresponding to substantially ½tp in synchronism with the sampling pulse $SP_1$ as shown in FIG. 7C. This signal $S_{12}$ is supplied to the counter 40 as the enable signal thereof.

The counter 40 counts the pulse length of the signal $S_{13}$ from the comparator 37 during the period in which the signal $S_{12}$ is at high level. On the other hand, the data selector 41 responds to the signals $S_1'$ and $S_4$ which are respectively shown in FIGS. 7A and 7B and selects.th data relating to the position detecting signal. If the selected data and the content of the counter 40 coincide with each other, the coincidence detecting circuit 42 produces at its output side a signal $S_{14}$ which continues from the trailing edge of the final pulse of the signal $S_{13}$ by a predetermined time as shown in FIG. 7E. This signal $S_{14}$ is supplied to the flip-flop circuit 47 as the data thereof.

The delay circuit 46 produces a signal $S_{15}$ in synchronism with the sampling pulse $SP_1$ with a delay of a predetermined time $\Delta t1$ therefrom as shown in FIG. 7F. This signal $S_{15}$ is supplied to the clock terminal CK of the flip-flop circuit 47, in which the signal $S_{14}$ supplied to the input terminal D thereof is latched. In this case, the delay time $\Delta t1$ of the delay circuit 46 is selected to satisfy the condition of $tp > \Delta t1 > tp/2$.

The delay circuit 45 produces a signal $S_{16}$ in synchronism with the sampling pulse $SP_{12}$, and delayed with respect thereto by a predetermined time $\Delta t2$ as shown in FIG. 7G. This signal $S_{16}$ is supplied to the counter 40 to thereby clear the content thereof and also supplied to the flip-flop circuit 47 to thereby reset the same. As a result, at the output side of the flip-flop circuit 47, there is produced a signal $S_{17}$ as shown in FIG. 7I. In this case, the delay time $\Delta t2$ of the delay circuit 45 is selected so as to satisfy the condition of $\Delta t2 > tp$.

Further, the delay circuit 43 produces a signal $S_{18}$ in synchronism with the sampling pulse $SP_1$ after therefrom by a predetermined time tp shown in FIG. 7J. This signal $SP_{18}$ is supplied to one input terminal of the AND circuit 48. Since the AND circuit 48 is supplied at the other input terminal thereof with the signal $S_{17}$ which is formed as described above, this signal $S_{17}$ is supplied to the AND circuit 48 as its substantially gate signal so as to open the gate thereof so that in response to the signal $S_{18}$, the sampling pulse $SP_2$ as shown in FIG. 7K is produced. This sampling pulse $SP_2$ is supplied to the sample-and-hold circuit 32.

In this way, the sampling pulse $SP_2$ can be produced.

In this case, the sampling pulse $SP_2$ can be produced by the data processing of a microcomputer (not shown).

This will be described with reference to the flow chart of FIG. 8.

Reference to FIG. 8, when the recording apparatus is set in a playback mode at step 100, the program goes to step 110 in which the position detecting signals S and T are detected. If they are not detected, the detecting operation is repeated at step 110 until the position detecting signals S and T are detected. If the position detecting signals S and T are detected at step 110, the first sampling pulse $SP_1$ is produced on the basis of the position detecting signals S and T at step 120 and the pulse Ni of the first sampling pulse $SP_1$ is counted during only the detection periods of the position detecting signals S and T at step 130.

Then, the program goes to the next step 140 in which it is judged whether the detected position detecting signals S and T are those which are produced first in the playback mode or not. If they are the first ones, the program goes to step 150 in which it is judged whether the interval is the interval $\frac{1}{2}tp$ or not and $\frac{1}{4}tp$ or not. If the interval satisfies either of them, the program goes to step 160 in which the second sampling pulse $SP_2$ is produced. If neither of the $\frac{1}{2}tp$ interval nor $\frac{1}{4}tp$ interval are satisfied at step 150, they are not the position detecting signals S and T so that the program returns to the step 110.

If at step 140 it is judged that the position detecting signals S and T are ones which are produced in the second time after the apparatus was set in the playback mode, the program goes to step 170 in which it is judged whether the polairy of the signal $S_4$ is changed or not. If the polarity of the signal $S_4$ is changed, the program goes to step 180 in which it is judged whether the preceding detection interval is $\frac{1}{2}tp$ or $\frac{1}{4}tp$. If it is $\frac{1}{2}tp$, the program goes further to step 190 in which it is judged whether the interval of the present position detecting signal is $\frac{1}{4}tp$ or not. If it is $\frac{1}{4}tp$, the position detecting signal is the true position detecting signal so that at step 160, the second sampling pulse $SP_2$ is produced. If on the other hand it is not $\frac{1}{4}tp$, the program returns to step 110.

If it is judged that the preceding detecting interval is $\frac{1}{4}tp$ at step 180, the program goes to step 200 in which it is judged whether the interval of the present position detecting signal is $\frac{1}{2}tp$ or not. If it is $\frac{1}{2}tp$, it is the true position detecting signal so that the program returns to step 160 in which the second sampling pulse $SP_2$ is produced. If on the other hand it is not $\frac{1}{2}tp$, the program returns to step 110.

The operations of the steps 170 to 200 will be described in detail with reference to FIGS. 5B, 5E and 5F. At step 170, if it is judged that the polarity of the signal $S_4$ is changed at the central portion of, for example, FIG. 5B, the program goes to step 180 in which it is judged whether $T_{B4}$ of the signal $S_{11}$ shown in FIG. 5F is $\frac{1}{2}tp$ or not and $\frac{1}{4}tp$ or not. Since it is $\frac{1}{2}p$, the program goes to step 190. At step 190, it is judged whether $S_{A3}$ of the signal $S_{10}$ shown in FIG. 5E is $\frac{1}{4}tp$ or not. Since it is $\frac{1}{4}tp$, the program goes to step 160 in which the second sampling pulse $SP_2$ is produced. At step 190, if the signal $S_{A3}$ is not $\frac{1}{4}tp$, the program returns to step 110.

At step 180, if $T_{B4}$ is $\frac{1}{4}tp$, it is judged that it is not the $T_{B4}$ of the signal $S_{11}$ but the signal $T_{B6}$ (accordingly, the time point at which the polarity of the signal $S_4$ is changed is not the central portion of FIG. 5B but the right hand end portion thereof), the program goes to step 200. At step 200, it is judged whether $S_{A5}$ (not shown) of the signal $S_{10}$ shown in FIG. 5E is $\frac{1}{2}tp$ or not. Since it should be $\frac{1}{2}tp$, the second sampling pulse $SP_2$ is produced at step 160. If at step 200 it is judged that the signal $S_{A5}$ is not $\frac{1}{2}tp$, the program returns to step 110.

If at step 170 the polarity of the signal $S_4$ is not changed, the program goes to step 210 at which it is judged whether the detecting interval is the same as the preceding position detecting signal or not. If it is the same, the program returns to step 160 at which the second sampling pulse $SP_2$ is produced. This will be described with reference to FIG. 5E. Since, for example, the first and second pulses $S_{A1}$ and $S_{A2}$ of the position detecting signal $S_{10}$ are same as $\frac{1}{2}tp$, the second sampling pulse $SP_2$ is produced at step 160. Then, if, at step 210, it is judged that the detecting intervals thereof are not equal to each other, such detection is regarded as the mis-detection and hence the first sampling state is maintained and the program returns to step 110.

As described above, by the signal processing of the microcomputer, it becomes possible to produce the second sampling pulse $SP_2$.

While in the above embodiment the rotary head assembly is such a special one that a tape is wound over an angular range narrower than an angular spacing of the heads to thereby carry out the recording and the reproducing, it is needless to say that this invention can be applied to a rotary head assembly in which the tape is wrapped over an angular range same as the angular spacing of the heads in the ordinary way.

As set forth above, according to this invention, when the recorded track is traced by a rotary head, a plurality of position detecting signals which are different in frequency between the adjacent tracks and different in recording length between the tracks relative to the same frequency are recorded on every predetermined track, the beginning end of these position detecting signals are taken as a reference so as to form a pulse signal which detects the pilot signal, and the tracking control of the rotary head is carried out by the tracking control signal based on the detected output. Accordingly, even if the apparatus has a mechanical secular variation, a temperature change or a jitter, without being affected by these parameters, it is possible to carry out the tracking control with good precision even when the apparatus for playback mode is different from that of the recording mode and also it is possible to present the compatibility between the apparatus.

Further, since the position detecting signals are different in frequency between the adjacent tracks, it is free of the influence of the crosstalk component and it is possible to widen a range in which the threshold level for detecting the position detecting signal is set.

Furthermore, since the position detecting signals are different in recording length between the adjacent tracks, the adjacent tracks can be discriminated from each other and it becomes possible to detect the position detecting signals in spite of a track displacement of a wide range.

In addition, since the position detecting signal for detecting the position of the tracking control pilot signal is recorded so as to have a beginning end near the center of the adjacent pilot signals, it becomes unnecessary to provide a circuit and the like for delaying the position detecting signal so as to place such beginning end near the center of the pilot signal, thus the circuit arrangement being simplified by that much.

The above description is given on a single preferred embodiment of the invention but it will be apparent that many modifications and variations could be effected by one skilled in the art without departing from the spirits or scope of the novel concepts of the invention so that the scope of the invention should be determined by the appended claims only.

We claim as our invention:

1. A method of recording digital signals on a record medium using a rotary head that periodically traces the record medium, the method comprising the steps of;
   recording a digital information signal in first areas of a plurality of contiguous respective slanted tracks formed on said record medium by said rotary head;
   determining second areas proximate each of the ends of said slanted tracks and different from said first areas;
   recording a tracking pilot signal in said second areas on said respective slanted tracks, whereby said tracking pilot signal is available for controlling tracking alignment of a playback head during reproduction of said information signal;
   determining as to each second area a reference position corresponding substantially to a center portion of said pilot signal as recorded on an adjacent track;
   determining as to each reference position a plurality of locations within the respective second area at predetermined positions relative to the respective reference position; and
   in the respective second areas, recording a corresponding plurality of position detecting signals having respective recording lengths and each of the position detecting signals beginning at a respective one of said locations.

2. A method of recording digital signals according to claim 1, in which each of said position detecting signals has a selected one of a plurality of different frequencies in different ones of said locations.

3. A method of recording digital signals according to claim 1, in which two of said position detecting signals are recorded beginning at respective first and second locations in each of said second areas, the two position detecting signals having a first frequency and first and second respective recording lengths in alternate slanted tracks and having a second frequency and first and second respective recording lengths in each of the other slanted tracks.

4. A method of recording digital signals according to claim 1, further comprising the steps of:
   tracing a track recorded by said rotary head with a playback head;
   reproducing the tracking pilot signal recorded on both tracks adjacent to said track being traced;
   reproducing the position detecting signals recorded on said track being traced;
   generating sampling pulses in response to said reproduced position detecting signals;
   sampling said tracking pilot signals as reproduced from said tracks adjacent to said track being traced and comparing the levels thereof;
   generating a tracking signal in response to said comparison; and
   controlling a tracking alignment of said playback head in response to said tracking signal.

5. A method or recording digital signals according to claim 4, in which said step of generating said sampling pulses includes the steps of generating a first sampling pulse in response to a reproduced position detecting signal, and generating a second sampling pulse when the time following said reproduced position detecting signal is substantially correspondent to a recording length of said pilot signal.

6. An apparatus for recording digital signals on a record medium using a rotary head that periodically traces the record medium, the apparatus comprising:
   means for recording a digital information signal in first areas of a plurality of contiguous respective slanted tracks formed on said record medium by said rotary head;
   means for determining second areas proximate each of the ends of said slanted tracks and different from said first areas;
   means for recording a tracking pilot signal in said second areas on said respective slanted tracks, whereby said tracking pilot signal is available for controlling tracking alignment of a playback head during reproduction of said information signals;
   means for determining as to each second area a reference position corresponding substantially to a center portion of said pilot signal as recorded on an adjacent track and a plurality of locations within the respective second area and having predetermined positions relative to the respective reference position; and
   means for recording, in the respective second areas, a corresponding plurality of position detection signals having respective recording lengths and each of the positon detecting signals beginning at a respective one of said locations.

7. An apparatus for recording digital signals according to claim 6, in which said means for recording the position detecting signals includes means for generating a plurality of recording frequencies.

8. An apparatus for recording digital signals according to claim 6, in which said means for recording the position detecting signals includes means for generating a first recording frequency during recording periods in first pulses having first and second lengths and means for generating a second recording frequency during recording periods in second pulses having first and second lengths, said first pulses being recorded in alternate slanted tracks and said second pulses being recorded in each of the other slanted tracks.

9. An apparatus for recording digital signals according to claim 6, further comprising:

means for tracing a track recorded by said rotary head and reproducing the tracking pilot signal and position detecting signals;

means for generating sampling pulses in response to said reproduced position detecting signals;

means for sampling said reproduced tracking pilot signals as reproduced from said tracks adjacent to said track being traced and comparing the levels thereof;

means for generating a tracking signal in response to said comparison; and means for controlling a tracking alignment of said playback head in response to said tracking signal.

10. An apparatus for recording digital signals according to claim 9, in which said means for generating sampling pulses includes means for generating first sampling pulses in response to said reproduced position detecting signals, and means for generating second sampling pulses on each occasion when the time following said reproduced position detecting signals is substantially correspondent to recording length of said pilot signal.

11. An apparatus for reproducing digital signals recorded on a record medium using a rotary head that periodically traces the record medium, the apparatus comprising:

means for reproducing a digital information signal recorded in first areas of a plurality of contiguous respective slanted tracks formed on said recording medium;

means for reproducing a tracking pilot signal recorded in second areas proximate both the ends of said respective slanted tracks and different from said first areas;

means for reproducing from each second area a plurality of position detection signals having respective recording lengths beginning at respective locations each having one of a plurality of predetermined relations to a reference position within the respective second area corresponding substantially to a center portion of said pilot signal as recorded on an adjacent track;

means for generating sampling pulses in response to said reproduced position detection signals;

means for sampling at times determined by said sampling pulses said tracking pilot signals as reproduced from said tracks adjacent to said track being traced and comparing reproduced levels thereof;

means for generating a tracking signal in response to the comparison; and means for controlling a tracking alignment of said head in response to said tracking signal.

* * * * *

UNITED STATES PATENT AND TRADEMARK OFFICE
CERTIFICATE OF CORRECTION

PATENT NO. : 4,739,420

DATED : April 19, 1988

INVENTOR(S) : Kentaro Odaka et al.

Page 1 of 2

It is certified that error appears in the above-identified patent and that said Letters Patent are hereby corrected as shown below:

Column 4, line 57, delete "," first occurence;

line 58, change "detai1" to --detail--.

Column 5, line 21, change "serv" to --servo--;

line 61, change "$S_6$" to -- $S_3$ --;

line 63, delete ":".

Column 6, line 5, change "druation" to --duration--.

Column 8, line 16, after "," insert --the--;

line 30, change "tne" to -- the --.

Column 9, line 18, after "$A_{T2}$" insert -- (Fig.3) --.

Column 10, line 52, change "$P_{B4}$" first occurence to --$P_{B3}$--.

Column 11, line 36, chansge "$P_{A1}$ and $P_{A2}$" to --$P_{A3}$ and $P_{A1}$;--.

Column 12, line 38, change "$SP_2$" to --$SP_1$--;

line 53, change ".th" to -- the --.

Column 13, line 2, change "$SP_{12}$" to --$SP_1$--.

UNITED STATES PATENT AND TRADEMARK OFFICE
CERTIFICATE OF CORRECTION

PATENT NO. : 4,739,420

DATED : April 19, 1988

INVENTOR(S) : Kentaro Odaka et al

It is certified that error appears in the above-identified patent and that said Letters Patent is hereby corrected as shown below:

IN CLAIMS.

Column 18, line 5, change "recording" to -- record --.

Signed and Sealed this

Twenty-fourth Day of January, 1989

Attest:

DONALD J. QUIGG

Attesting Officer

Commissioner of Patents and Trademarks